United States Patent [19]
Goodrich, Jr. et al.

[11] Patent Number: 5,153,004
[45] Date of Patent: Oct. 6, 1992

[54] FREEZING AND THAWING OF ERYTHROCYTES

[75] Inventors: Raymond P. Goodrich, Jr.; Christine M. Williams, both of Pasadena, Calif.

[73] Assignee: Cryopharm Corporation, Pasadena, Calif.

[21] Appl. No.: 505,255

[22] Filed: Apr. 5, 1990

Related U.S. Application Data

[63] Continuation-in-part of Ser. No. 361,023, Jun. 2, 1989, abandoned.

[51] Int. Cl.⁵ .............................................. A61K 35/18
[52] U.S. Cl. .................................... 424/533; 435/2
[58] Field of Search ........................... 435/2; 424/533

[56] References Cited
U.S. PATENT DOCUMENTS
4,980,277 12/1990 Junnila .................................... 435/1

OTHER PUBLICATIONS
Myhrvold–Acta Vet. Scand–vol. 20, (1979) pp. 525–530.
Sakaida, et al., Ann. N.Y. Acad. Sci., 125:647 (1964).
Richards, et al. Am. J. Surg., 108:313 (1964).

*Primary Examiner*—Sam Rosen
*Attorney, Agent, or Firm*—Heller, Ehrman, White & McAuliffe

[57] ABSTRACT

A process and medium are disclosed for the freezing of red blood cells which comprises the use of solutions including monosaccharide hexoses and pentoses, and/or biocompatible amphipathic polymers to permit the thawing without washing to produce viable red blood cells.

14 Claims, No Drawings

FREEZING AND THAWING OF ERYTHROCYTES

This application is a continuation-in-part of Ser. No. 361,023, filed Jun. 2, 1989, now abandoned.

FIELD OF THE INVENTION

This invention relates to the general field of biochemistry and medical sciences, and specifically to processes for the preservation by freezing, storage and thawing of red blood cells without washing.

BACKGROUND AND SUMMARY OF THE INVENTION

Blood is a major tissue of the human body, and has as a predominant role the delivery of oxygen from the lungs to peripheral tissues. This role is carried out by erythrocytes, i.e., red blood cells (RBC). The oxygen is furnished to the peripheral cells by an exchange-diffusion system brought about in the lungs in a red, iron-containing protein called hemoglobin. When hemoglobin combines with oxygen, oxyhemoglobin is formed and after oxygen is given up by the tissues, the oxyhemoglobin is reduced to deoxyhemoglobin.

The red cell membrane is composed of two major structural units, the membrane bilayer and a cytoskeleton. A lipid bilayer and integral membrane proteins form the membrane bilayer, which has little structural strength and fragments readily by vesiculation. The other major component, the membrane skeleton, stabilizes the membrane bilayer and provides resistance to deformation. The cytoskeleton is linked to the bilayer in the erythrocyte membrane, possibly by lipid-protein as well as protein-protein associations. The hemoglobin, and other RBC components, are contained within the red cell membrane.

In adults, bone marrow is active in the formation of new red blood cells. Once erythrocytes enter the blood, they have an average lifetime of about 120 days. In an average person, about 0.83% of the erythrocytes are destroyed each day by phagocytosis, hemolysis or mechanical damage in the body, and the depleted cells are renewed by the bone marrow.

A wide variety of injuries and medical procedures require the transfusion of whole blood or a variety of blood components. Every patient does not require whole blood and, in fact, the presence of all of the blood components can cause medical problems. Separate blood fractions can be stored under those special conditions best suited to assure their biological activity at the time of transfusion. For example, when donor blood is received at a processing center, erythrocytes are separated and stored by various methods. Such cells are storable in citratephosphate-dextrose at 4° C. for up to five weeks, generally as a unit of packed erythrocytes having a volume of from 200 to 300 ml and a hematocrit value (expressed as corpuscular volume percent) of 70 to 90.

Erythrocytes may also be frozen at from $-30°$ C. to $196°$ C. and stored for up to seven years in a glycerol solution, but must be kept frozen at low temperatures in order to survive sufficiently for transfusion. Both these methods require careful maintenance of storage temperature to avoid disruption of the desired biological activity of the erythrocytes, and must meet the American Association of Blood Bank (AABB) standard of survival of 80–85% of the thawed cells. After thawing the cells must be washed to remove the glycerol, which is a time and cost disadvantage.

It has thus been a desideratum to obtain a method for the storage of red blood cells which does not require the washing of the thawed cells prior to transfusion. Such a method would facilitate the rapid availability of erythrocytes for medical purposes.

One such desired method has been the freezing of red blood cells, since such cells could be stored and easily reconstituted for use in mammals.

The process of the present invention allows for the freezing, then thawing of erythrocytes without washing under conditions which maintain structure of the cell and the biological activity of the hemoglobin, and which permits the reconstitution of the red blood cells to allow use on a therapeutic level. Briefly, the process comprises immersing a plurality of erythrocytes in a physiologic buffered aqueous solution containing a carbohydrate and a polymer having amphipathic properties and freezing the solution to yield frozen erythrocytes which, when thawed, produce without washing a significant percentage of intact and viable red blood cells. By the term amphipathic, it is meant that there are hydrophilic and hydrophobic portions on a single molecule.

The carbohydrate of the invention is biologically compatible with the RBCs, that is, non-disruptive to the cells, and one which permeates, or is capable of permeating, the membrane of the erythrocytes. The carbohydrate may be selected from the group consisting of monosaccharides, since disaccharides do not permeate the membrane to any significant extent. Monosaccharide pentoses and hexoses are preferred in concentrations from about 0.2 to about 4.0 molar, preferably about two molar. Xylose, glucose, ribose, mannose and fructose are employed to particular advantage.

In another aspect of the invention, the addition to the carbohydrate solution of a water soluble, biologically compatible polymer having amphipathic properties adds significantly to the percentage of biologically-active hemoglobin which is retained in the cells and recovered after thawing of red blood cells. The polymer may be present in the solution in concentrations of from 0.1 millimolar up to saturation. The polymers may have a molecular weight in the range of about 1K to about 360K. Preferably, the polymer has a molecular weight of at least about 2.5K, most preferably from about 20K to 50K, and is present in a concentration of from about 5% up to the limit of solubility of the polymer in the solution. Polymers selected from the group consisting of polyvinylpyrrolidone (PVP) and polyvinylpyrrolidone derivatives, and dextran and dextran derivatives, provide significant advantages. Other amphipathic polymers may be used, such as poloxamers in any of their various forms. Amino acid based polymers (i.e., proteins) or hydroxyethyl starch may also be employed. The use of the carbohydrate-polymer solution in the lyophilization of red blood cells allows for the recovery of intact cells, a significant percentage of which contain biologicallyactive hemoglobin. While not intending to be bound by any theory, the amphipathic properties of the polymer allow them to bind to the cell membrane while protecting the membrane surface by extension of the hydrophilic portion into the aqueous environment. This may alleviate the damage to the cell membrane which causes other problems, such as cell aggregation.

The described solutions provide media which permit red blood cells to be subjected to the stresses of freezing, and thawing to yield cells which are capable of functioning normally in mammals. Unless indicated otherwise by the terminology or the context, all percentages set forth herein are expressed as weight percentages.

As noted above, the process of the invention provides a medium for the freezing and thawing without washing of intact and biologically-active erythrocytes. While the media of the invention are novel, it will be understood that apparatus and related techniques are known by those of skill in the art for the lyophilization of various materials, and cells in particular, and only the specific temperatures and apparatus employed in the examples are described herein. From this description, one of ordinary skill in the art will be capable of employing the media of the invention in a process for the freezing and thawing without washing of intact, viable red blood cells.

EXAMPLE 1

Red blood cells were washed 3 times in phosphate buffered saline (PBS:10 mM phosphate+150 mM NaCl) prior to mixing with the freezing buffer described below. The freezing solution was added to the cells at 10, 30, 40 and 50% hematocrits at room temperature. The freezing buffer consisted of 1.6M glucose and 16% PVP (M.W. 40K), 1.9M glucose and 19% PVP, and 2.25M glucose and 22.5% PVP, 2.6M glucose and 26% PVP as the initial concentration, respectively. The final concentrations for all hematocrits after mixing were then 1.47M glucose and 14.7% PVP. The samples were frozen initially at −60° C., then at −196° C. The samples were frozen 24 hrs at −80° C. After 24 hrs, the samples were thawed at 37° C. The cells were analyzed according to hemoglobin recovery, hemoglobin preservation, ATP concentration and RBC indices.

| Table of Hemoglobin Recoveries | | |
|---|---|---|
| Hematocrit | % Hemoglobin Recovery | HB ATP |
| 10 | 67.16% | 2.47 |
| 30 | 56.47 | 2.31 |
| 40 | 54.03 | 2.07 |
| 50 | 53.02 | 2.03 |

| Table of Hemoglobin Preservation | | | |
|---|---|---|---|
| Hematocrit | % OxyHb | % MetHB | % Hemochrome |
| 10 | 90.0 | 3.78 | 5.31 |
| 30 | 96.23 | 3.77 | 0 |
| 40 | 95.87 | 2.50 | 1.63 |
| 50 | 96.21 | 3.50 | 0.29 |

| Table of RBC Indices | | | |
|---|---|---|---|
| Hematocrit | MCV (cum) | MCH (pg) | MCHC (%) |
| 10 | 112.3 | 30.5 | 27.1 |
| 30 | 128.2 | 31.2 | 24.3 |
| 40 | 127.4 | 30.2 | 23.7 |
| 50 | 120.5 | 32.8 | 27.3 |

EXAMPLE 2

Red blood cells were washed 3 times in PBS prior to mixing with freezing buffer. The freezing buffer contained 0.8M glucose and 16% PVP (M.W. 40K) as the initial concentrations. The sample was mixed and frozen at a 50% hematocrit in liquid nitrogen, then thawed at 37° C. The recovery was measured according to 51-Cr labeling. The cells were labeled before freezing. After thawing at 37° C., the cells were diluted in autologous whole blood to determine the in vitro stability versus time.

A second sample was prepared according to the method above, but containing a formulation in the freezing buffer of 8% PVP (M.W. 40K) as the initial concentration.

| Table of Recoveries Before and After Freezing | | |
|---|---|---|
| Sample | Before Freezing | After Freezing |
| 0.8M glucose + 16% PVP | 98.4% | 86.1% |
| 8% PV | 99.3% | 83.9% |

| Table of Recoveries for Whole Blood Stability Percent Recovery vs. Time | | | |
|---|---|---|---|
| Sample | 30 Minutes | 60 Minutes | 18 Hours |
| 0.8M glucose + 16% PVP | 61.5 | 59.8 | 59.2 |
| 8% PVP | 61.8 | 64.1 | 52.0 |

| Table of Net Recoveries After 18 Hours in Whole Blood | | | |
|---|---|---|---|
| Sample | Freeze-Thaw | Incubation | Net |
| 0.8M glucose + 16% PVP | 86.1% | 68.8% | 59.2% |
| 8% PVP | 83.9% | 62.0% | 52.0% |

EXAMPLE 3

Red blood cells were washed 3 times in PBS prior to mixing with the freeezing buffer. The freezing buffer contained a 0.5-2M initial concentrations of a free carbohydrate in PBS. The samples were prepared using a 10% hematocrit. The samples were then frozen at −15° C. or at −196° C. The samples were thawed at 37° C. and analyzed according to pellet recovery.

| Table of Pellet Recoveries of RBCs Frozen in Free Carbohydrate | | |
|---|---|---|
| Carbohydrate | −15° C. | −196° C. |
| untreated (no carb.) | − | − |
| maltose | +/− | − |
| trehalose | + | +/− |
| glucose | + | +/− |
| sucrose | − | − |
| galactose | − | − |
| maltotriose | +/− | +/− |

+ good pellet recovery
+/− fair pellet recovery
− poor pellet recovery

WHAT IS CLAIMED IS:

1. A process for storing a composition consisting essentially of washed human erythrocytes having a cell membrane, comprising immersing washed erythrocytes in a solution which includes a monosaccharide, which is capable of permeating the membrane of the erythrocytes, in a concentration of from about 0.2 to about 4 molar; and freezing said solution and erythrocytes.

2. A process according to claim 1 further comprising the step of thawing said solution and erythrocytes.

3. The process of claim 1 wherein the monosaccharide is selected from the group consisting of pentose and hexose.

4. The process of claim 1 or 2 wherein the monosaccharide is selected from the group consisting of xylose, glucose, ribose, mannose and fructose.

5. The process of claim 4 wherein the monosaccharide is present in the solution in a concentration of about 2 molar.

6. A process for storing a composition consisting essentially of washed erythrocytes, comprising:
immersing washed erythrocytes in a water solution which includes:
a monosaccharide which is present in the solution in a concentration of from about 0.5 molar up to about 4 molar, and
an amphipathic polymer having a molecular weight of from about 1K to about 360K which is present in a concentration of from about 0.1 millimolar up to saturation in the solution; and
freezing said solution and erythrocytes.

7. A process according to claim 6 further comprising the step of thawing said solution and erythrocytes.

8. The process of claim 6 or 7 wherein the monosaccharide is selected from the group consisting of pentoses and hexoses.

9. The process of claim 6 or 7 wherein the monosaccharide is selected from the group consisting of xylose, glucose, ribose, mannose and fructose.

10. The process of claim 6 or 7 wherein the polymer is selected from the group consisting of polyvinylpyrrolidone and dextran.

11. The process of claim 6 or 7 wherein the polymer is polyvinylpyrrolidone.

12. A composition comprising reconstituted erythrocytes produced according to the process of claim 2 or 7.

13. A composition of frozen erythrocytes produced according to the process of claim 1 or 6.

14. A process according to claim 6 wherein said amphipathic polymer has a molecular weight of at least about 2.5K.

* * * * *

UNITED STATES PATENT AND TRADEMARK OFFICE
CERTIFICATE OF CORRECTION

PATENT NO. : 5,153,004
DATED : October 6, 1992
INVENTOR(S) : Raymond P. Goodrich It is certified that error appears in the above-indentified patent and that said Letters Patent is hereby corrected as shown below:

Column 1, line 5, after "abandoned", add --which is a continuation-in-part of 07/195,745, filed May 18, 1988--

Signed and Sealed this

Twelfth Day of October, 1993

Attest:

BRUCE LEHMAN

*Attesting Officer*  *Commissioner of Patents and Trademarks*